(12) United States Patent
McLean et al.

(10) Patent No.: US 12,303,402 B2
(45) Date of Patent: May 20, 2025

(54) SPINAL INTERBODY FUSION DEVICE

(71) Applicant: SPINE WAVE, INC., Shelton, CT (US)

(72) Inventors: Scott McLean, Sandy Hook, CT (US);
Haibo Fan, Woodbridge, CT (US);
Steven Wolfe, Juno Beach, FL (US)

(73) Assignee: SPINE WAVE, INC., Shelton, CT (US)

( * ) Notice: Subject to any disclaimer, the term of this patent is extended or adjusted under 35 U.S.C. 154(b) by 0 days.

(21) Appl. No.: 18/928,481

(22) Filed: Oct. 28, 2024

(65) Prior Publication Data

US 2025/0049581 A1 Feb. 13, 2025

Related U.S. Application Data

(63) Continuation of application No. 18/486,622, filed on Oct. 13, 2023, now Pat. No. 12,161,565, which is a (Continued)

(51) Int. Cl.
*A61F 2/44* (2006.01)
*A61F 2/30* (2006.01)
*A61F 2/46* (2006.01)

(52) U.S. Cl.
CPC .... *A61F 2/447* (2013.01); *A61F 2002/30593* (2013.01); *A61F 2002/3093* (2013.01);
(Continued)

(58) Field of Classification Search
CPC .. A61F 2/442; A61F 2/447; A61F 2/44; A61F 2002/30593; A61F 2002/3093; A61F 2002/4629; A61F 2310/00023
(Continued)

(56) References Cited

U.S. PATENT DOCUMENTS

| | | |
|---|---|---|
| 4,932,969 A | 6/1990 | Frey et al. |
| 5,002,576 A | 3/1991 | Fuhrmann et al. |
| (Continued) | | |

FOREIGN PATENT DOCUMENTS

| | | |
|---|---|---|
| DE | 90 00 094 U1 | 1/1991 |
| EP | 1605872 B1 | 9/2009 |

OTHER PUBLICATIONS

Drake Medical Plastics, "What Benefits Do PEEK Spinal Cages Offer Patients?", 5 pages, Copyright 2021.
(Continued)

*Primary Examiner* — Jessica Weiss
(74) *Attorney, Agent, or Firm* — Hoffmann & Baron, LLP

(57) ABSTRACT

A bellows shaped spinal implant, comprising an upper plate, a lower plate and a bellows shaped shell extending between and joining the upper and lower plates. The bellows shaped shell is formed of titanium or an alloy comprising titanium and includes a wall extending therearound that defines a hollow interior. The wall has a thickness in the range of 0.5 mm to 1.0 mm to provide for radiographic imaging through the wall. The wall is angled or curved inwardly or outwardly between the upper and lower plates to provide stiffness mimicking the stiffness properties of a similarly sized polyetheretherketone (PEEK) implant. The upper and lower plates each comprise porous contact regions including a three-dimensional gyroid lattice structure defined by a plurality of struts and pores in communication with the hollow interior. The outer surfaces of at least a portion of the struts may comprise a laser ablated textured surface.

29 Claims, 13 Drawing Sheets

Related U.S. Application Data continuation of application No. 18/087,454, filed on Dec. 22, 2022, now Pat. No. 11,826,265, which is a continuation-in-part of application No. 17/847,873, filed on Jun. 23, 2022, now Pat. No. 11,701,241.

(60) Provisional application No. 63/215,593, filed on Jun. 28, 2021.

(52) U.S. Cl.
CPC .............. *A61F 2002/4629* (2013.01); *A61F 2310/00023* (2013.01)

(58) Field of Classification Search
USPC ............................................ 623/17.11–17.16
See application file for complete search history.

(56) References Cited

U.S. PATENT DOCUMENTS

| | | | |
|---|---|---|---|
| 5,282,861 A * | 2/1994 | Kaplan | B22F 3/114 623/23.51 |
| 5,473,138 A | 12/1995 | Singh et al. | |
| 5,674,294 A | 10/1997 | Bainville et al. | |
| 6,206,924 B1 | 3/2001 | Timm | |
| 6,264,695 B1 | 7/2001 | Stoy | |
| 6,395,032 B1 | 5/2002 | Gauchet | |
| 6,465,742 B1 | 10/2002 | Hiraoka et al. | |
| 6,527,804 B1 | 3/2003 | Gauchet et al. | |
| 6,579,320 B1 * | 6/2003 | Gauchet | A61F 2/30742 623/17.15 |
| 6,582,468 B1 | 6/2003 | Gauchet | |
| 6,981,989 B1 | 1/2006 | Fleischmann et al. | |
| 7,166,131 B2 | 1/2007 | Studer et al. | |
| 7,331,994 B2 | 2/2008 | Gordon et al. | |
| 7,578,848 B2 | 8/2009 | Albert et al. | |
| 7,585,324 B2 | 9/2009 | Albert et al. | |
| 7,892,285 B2 | 2/2011 | Viker | |
| 7,918,888 B2 | 4/2011 | Hamada | |
| 8,764,832 B2 | 7/2014 | Schwab et al. | |
| 8,945,228 B2 | 2/2015 | Popa et al. | |
| 9,370,609 B2 | 6/2016 | Grohowski, Jr. | |
| 9,987,051 B2 | 6/2018 | Nunley et al. | |
| 10,278,823 B1 | 5/2019 | Xue et al. | |
| 10,603,093 B2 | 3/2020 | Lin et al. | |
| 10,772,732 B1 | 9/2020 | Miller et al. | |
| 11,026,798 B1 | 6/2021 | Miller et al. | |
| 11,185,423 B2 | 11/2021 | Tipping | |
| 11,446,159 B2 | 9/2022 | Mirda et al. | |
| 11,771,528 B1 | 10/2023 | Robinson et al. | |
| 2002/0128716 A1 | 9/2002 | Cohen et al. | |
| 2003/0040801 A1 | 2/2003 | Ralph et al. | |
| 2003/0201578 A1 * | 10/2003 | Li | B23K 26/40 425/173 |
| 2004/0024407 A1 | 2/2004 | Ralph et al. | |
| 2005/0177238 A1 | 8/2005 | Khandkar et al. | |
| 2005/0197702 A1 * | 9/2005 | Coppes | A61F 2/441 623/17.13 |
| 2005/0228500 A1 | 10/2005 | Kim et al. | |
| 2006/0052872 A1 | 3/2006 | Studer et al. | |
| 2006/0149381 A1 | 7/2006 | Kim | |
| 2006/0200240 A1 | 9/2006 | Rothman et al. | |
| 2006/0241765 A1 | 10/2006 | Burn et al. | |
| 2007/0173940 A1 * | 7/2007 | Hestad | A61F 2/44 623/17.12 |
| 2009/0069895 A1 | 3/2009 | Gittings et al. | |
| 2009/0069896 A1 | 3/2009 | Reo | |
| 2009/0138088 A1 | 5/2009 | Scribner et al. | |
| 2009/0157185 A1 | 6/2009 | Kim | |
| 2011/0082552 A1 * | 4/2011 | Wistrom | A61F 2/4425 623/17.16 |
| 2011/0238185 A1 | 9/2011 | Filippi et al. | |
| 2012/0089227 A1 | 4/2012 | Jarzem | |
| 2012/0277861 A1 | 11/2012 | Steele et al. | |
| 2012/0312778 A1 | 12/2012 | Ullrich, Jr. et al. | |
| 2012/0316650 A1 * | 12/2012 | Ullrich, Jr. | A61F 2/4455 29/592 |
| 2015/0335434 A1 | 11/2015 | Patterson et al. | |
| 2017/0151004 A1 * | 6/2017 | Lin | A61B 17/846 |
| 2018/0104063 A1 | 4/2018 | Asaad | |
| 2018/0117533 A1 | 5/2018 | Arafat et al. | |
| 2018/0296343 A1 | 10/2018 | Wei | |
| 2018/0338838 A1 | 11/2018 | Cryder et al. | |
| 2019/0008651 A1 | 1/2019 | Doty | |
| 2019/0192303 A1 | 6/2019 | Gallagher et al. | |
| 2019/0343645 A1 | 11/2019 | Miccio et al. | |
| 2020/0138594 A1 | 5/2020 | Renganath et al. | |
| 2020/0197565 A1 | 6/2020 | Suh et al. | |
| 2020/0261243 A1 | 8/2020 | Unger et al. | |
| 2021/0316367 A1 * | 10/2021 | Padilla | B33Y 50/00 |
| 2022/0087670 A1 | 3/2022 | Selmoune | |
| 2022/0168809 A1 | 6/2022 | Seleznev et al. | |
| 2022/0233330 A1 | 7/2022 | Gray et al. | |
| 2022/0296386 A1 * | 9/2022 | Fang | A61F 2/447 |
| 2023/0414375 A1 | 12/2023 | Robinson | |

OTHER PUBLICATIONS

Barba, D. et al., "Synthetic bone: Design by additive manufacturing", Acta Biomaterialia, vol. 97, pp. 637-656, 2019.

Supplemental European Search Report for a counterpart foreign application dated Mar. 17, 2025.

* cited by examiner

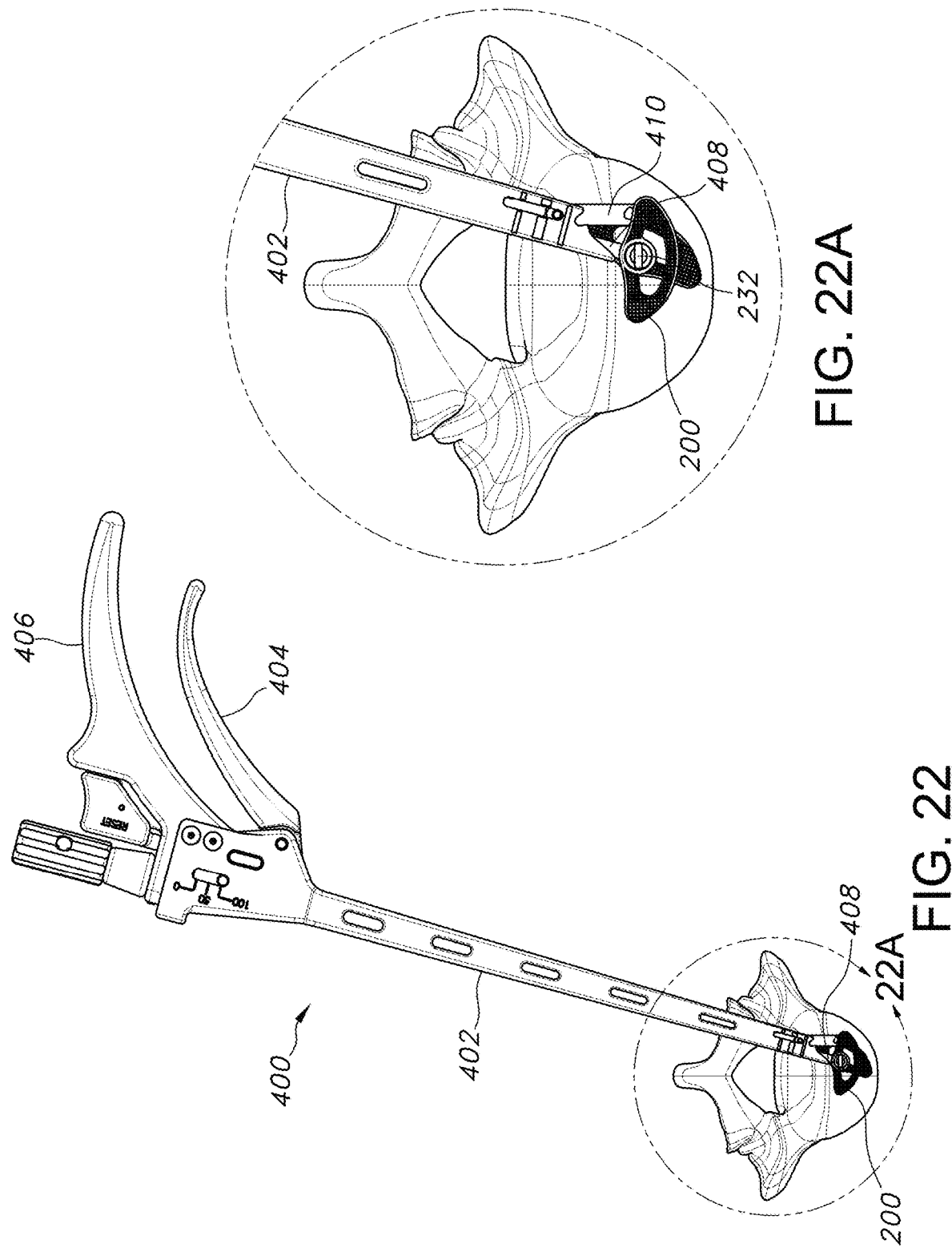

SPINAL INTERBODY FUSION DEVICE

CROSS-REFERENCE TO RELATED APPLICATION

This application is a continuation of U.S. application Ser. No. 18/486,622, filed Oct. 13, 2023, now U.S. Pat. No. 12,161,565, which is a continuation of U.S. application Ser. No. 18/087,454, filed Dec. 22, 2022, now U.S. Pat. No. 11,826,265, which is a continuation-in-part of U.S. application Ser. No. 17/847,873, filed Jun. 23, 2022, now U.S. Pat. No. 11,701,241, which claims the benefit of Provisional Patent Application No. 63/215,593, filed Jun. 28, 2021, each of which is incorporated herein by reference in its entirety.

FIELD OF THE INVENTION

The subject invention relates generally to the field of spinal implants and more particularly to a spinal interbody fusion device that is configured to mimic the biomechanical properties of the spine, provide radiolucency for radiographic observation of the fusion process, and for providing enhanced osteointegration to vertebral bodies intradiscally.

BACKGROUND OF THE INVENTION

Spinal implants such as interbody fusion devices are used to treat degenerative disc disease and other damages or defects in the spinal disc between adjacent vertebrae. The disc may be herniated or suffering from a variety of degenerative conditions, such that the anatomical function of the spinal disc is disrupted. Most prevalent surgical treatment for these conditions is to fuse the two vertebrae surrounding the affected disc. In most cases, the entire disc will be removed, except for a portion of the annulus, by way of a discectomy procedure. A spinal interbody fusion device is then introduced into the intradiscal space and suitable bone graft, or bone substitute material is placed substantially in and/or adjacent the device in order to promote fusion between two adjacent vertebrae.

Spinal interbody fusion devices, some of which are expandable and others of fixed dimension, may be used to treat spinal conditions in the cervical, thoracic and lumbar regions of the spine. In cervical fusion, such devices are introduced anteriorly while in thoraco-lumbar surgery, the device may also be inserted in a posterior, lateral or transforaminal approach. The particular approach selected is primarily determined by the type of treatment to be administered by the surgeon. In order to accommodate the spinal anatomy and promote arthrodesis, an interbody fusion device preferably mimics the biomechanical properties of the spine and optimizes contact to achieve osteointegration with adjacent endplates of opposing vertebral bodies.

In addition to the size and configuration of a spinal interbody fusion device, the materials used in the device are a significant factor for a successful spinal fusion procedure. While the material for a spinal interbody fusion device must be biocompatible, other properties to be considered include strength, stiffness, fatigue and radiolucency. For many years titanium has been a material of choice not only for its biocompatibility with the human body, but also because it is sturdy and strong and fuses readily with bone. While providing desirable osteointegration with bone, titanium has issues in providing required flexibility and resilience in the intradiscal space. Further, as titanium lacks sufficient radiolucency it often obscures attempts to image the surgical site. Synthetic materials have been developed over the recent years as an alternative to titanium, such as polyetheretherketone (PEEK). PEEK has physical properties that are similar to bone and is inherently translucent allowing imaging transparency. Unfortunately, PEEK does not provide osteointegration with bone. As a result, and in an effort to enhance fusion with bone, spinal implants formed of PEEK are sometimes coated with a titanium layer on the surfaces that interface with adjacent vertebral body endplates.

Accordingly, there is a still a desire to develop an interbody fusion device that beneficially combines the sturdiness, strength and osteointegration characteristics of titanium with the radiolucency and biomechanical properties of PEEK that are similar to bone.

SUMMARY OF THE INVENTION

It is an object of the invention to provide an additive manufactured bellows shaped spinal implant comprising a bellows shaped shell having a wall that is configured and dimensioned to achieve radiographic imaging therethrough, the wall being inwardly angled and dimensioned to provide stiffness that mimics the stiffness properties of a similarly sized polyetheretherketone (PEEK) implant.

It is another object of the invention to provide a bellows shaped spinal implant comprising upper and lower porous contact regions with gyroid lattice structures for contacting endplates of opposing vertebral bodies and for providing enhanced osteointegration thereto.

DESCRIPTION OF THE FIGURES

FIG. 22 is a view of the TLIF spinal implant of the subject invention mounted to an insertion tool with the spinal implant being shown in a rotated position within the intradiscal space.

FIG. 22A is an enlarged view of the encircled portion of FIG. 22.

DESCRIPTION OF THE EMBODIMENTS

Figure 1:
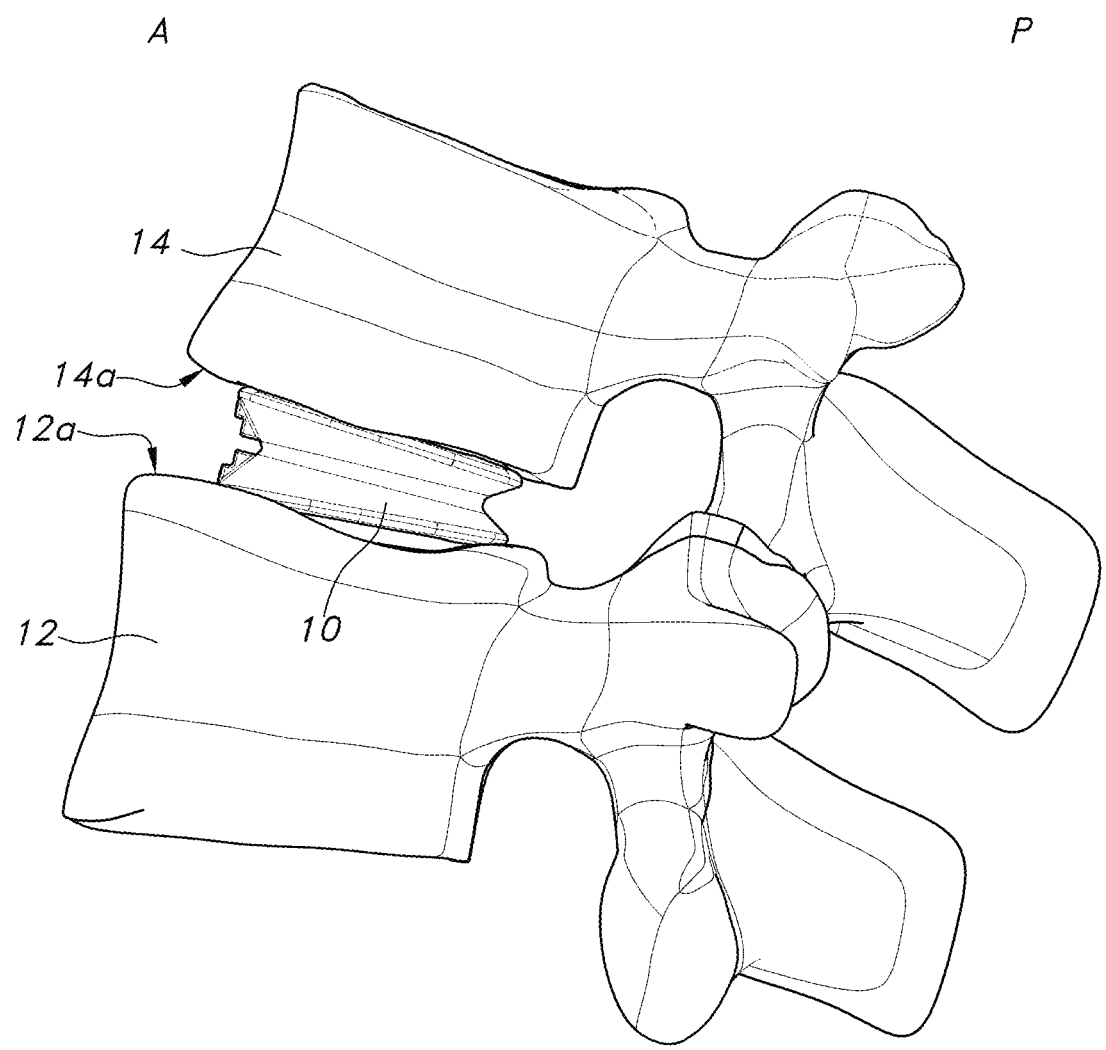
FIG. 1 is a lateral elevation view of a lumbar portion of a human spine with a bellows shaped spinal implant according to an embodiment of the present invention configured as an anterior lumbar interbody fusion device (ALIF) having been placed in position between two opposing vertebral bodies.

For the purposes of promoting and understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
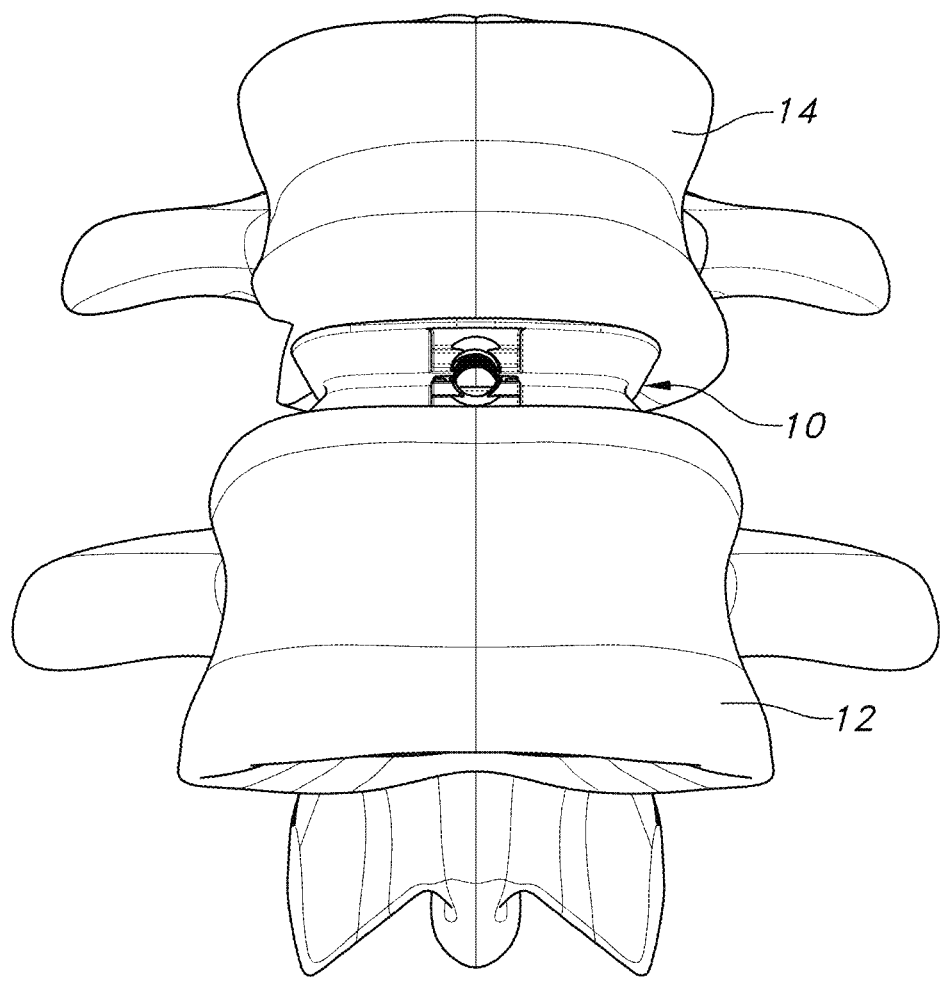
FIG. 2 is a view of FIG. 1 as seen from the anterior direction.

Referring to FIGS. 1 and 2, there is shown a segment of the lumbar region of a human spine into which a bellows shaped spinal implant 10 in accordance with a particular arrangement of the invention has been inserted. In this particular arrangement, spinal implant 10 is sized and configured as an anterior lumbar interbody fusion (ALIF) device that is introduced between opposing vertebral bodies 12 and 14 from an anterior (A) direction toward the posterior (P) portion of the spine. As shown, bellows shaped spinal implant 10 is a conventional ALIF device in that supplemental fixation in the form of plates and/or rods are used in conjunction with the spinal implant 10 to secure spinal implant 10 in place subsequent to insertion. As will be described, a bellows shaped spinal implant configured as a standalone version is also contemplated. It should be appreciated that bellows shaped spinal implant 10 may also be configured for insertion into other portions of the spine, such as the thoracic region and the cervical region.

Figure 3:
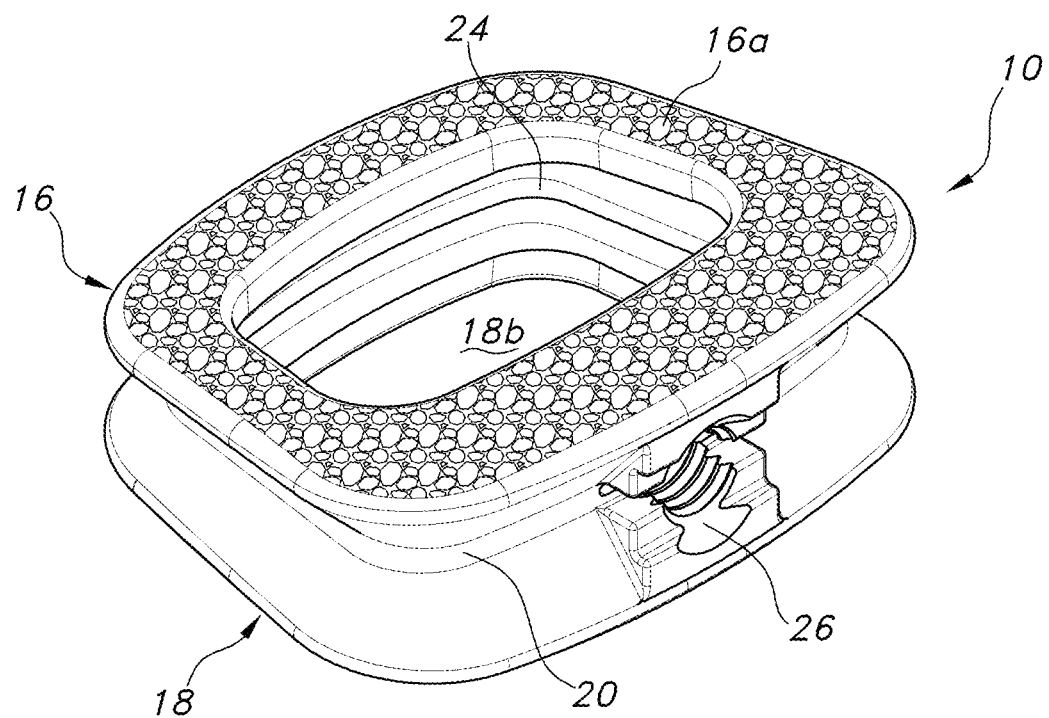
FIG. 3 is a top perspective view of the bellows shaped ALIF as seen from the anterior direction.
Figure 4:
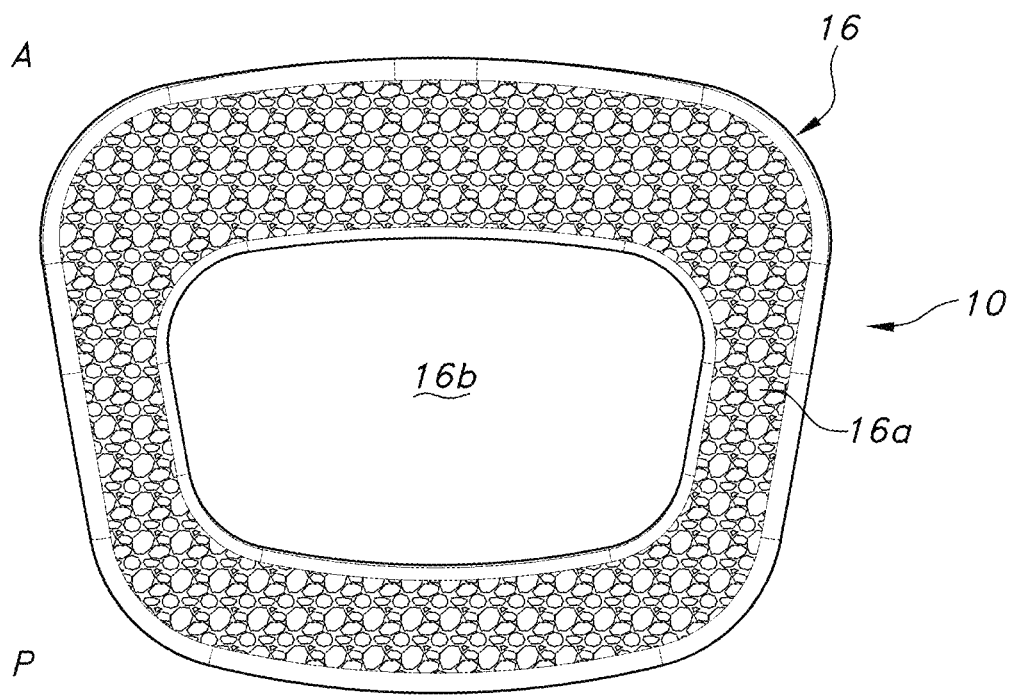
FIG. 4 is a top plan view of the bellows shaped ALIF device of FIG. 3.
Figure 5:
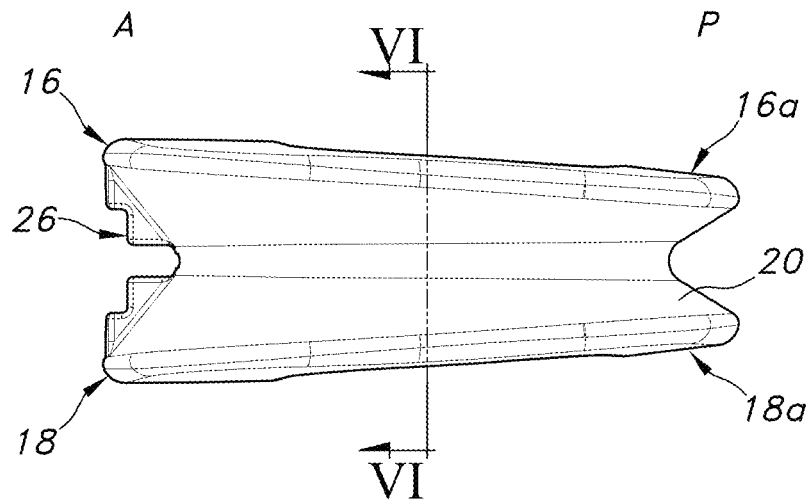
FIG. 5 is a lateral elevation view of the bellows shaped ALIF device of FIG. 3.
Figure 6:
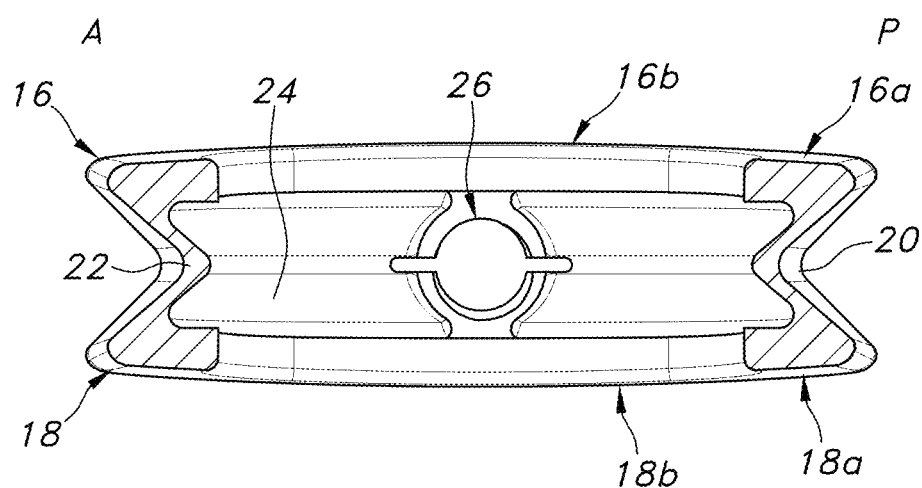
FIG. 6 is a cross-sectional view of the bellows shaped ALIF device as seen along viewing lines VI-VI of FIG. 5.

Turning now to FIGS. 3-8, details of the bellows shaped spinal implant 10 are described. Spinal implant 10 comprises an upper plate 16 and a lower plate 18 that are joined together by a bellows shaped shell 20. Upper plate 16 has a contact surface 16a configured to contact the endplate 14a of superior vertebral body 14 and lower plate 18 is a contact surface 18a configured to contact the endplate 12a of inferior vertebral body 12. Contact surfaces 16a and 18a may be generally planar and angled downwardly from the anterior (A) to the posterior (P) direction as illustrated in FIG. 5 so as to provide suitable lordosis upon insertion between vertebral bodies 12 and 14. Such a downward angle may be, for example, between 0 and 30 degrees. Contact surfaces 16a and 18a may be slightly curved along the lateral direction as illustrated in FIG. 6 so as to provide a more suitable anatomic contact with vertebral body endplates 14 and 16, respectively. As shown in FIGS. 3 and 4, lower plate 18 has a central opening 18b and upper plate 16 has a central opening 16b.

Figure 7:
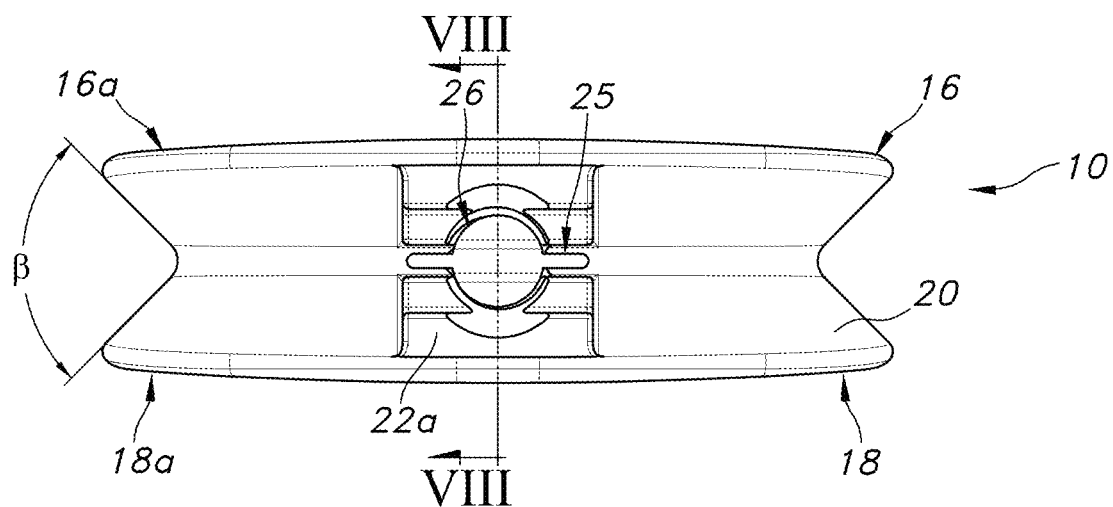
FIG. 7 is an anterior elevation view of the bellows shaped ALIF device of FIG. 3, the shell wall of the ALIF device being inwardly angled or curved.
Figure 8:
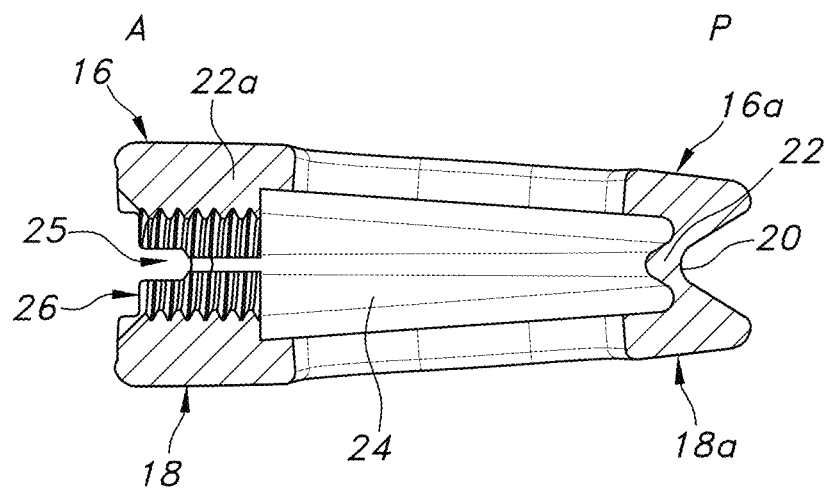
FIG. 8 is a cross-sectional view of the bellows shaped ALIF device as seen along viewing lines VIII-VIII of FIG. 7.

Shell 20, as seen more particularly in FIGS. 5-8, is configured to have a bellows shape having a relatively thin wall 22 extending around the periphery of shell 20, wall 22 defining a hollow interior 24. Hollow interior 24 provides a space for bone graft material and is in fluid communication with central opening 16b of upper plate 16 and with central opening 18b of lower plate 18. Wall 22 is angled or curved inwardly between upper plate 16 and lower plate 18 and flares outwardly in both directions toward upper plate 16 and lower plate 18, respectively. As such as shown in FIG. 7, an angle beta, β is formed in wall 22. Wall 22 may be provided with a relatively thicker portion 22a at the anterior (A) end as shown in FIGS. 7 and 8 through which a threaded hole 26 may be formed for insertion and graft delivery purposes, as will be described. In some instances, a suitable slit 25 or cut may be provided laterally into thicker portion 22a so as to minimize stiffening of implant 10. It should also be understood that wall 22 of bellows shaped shell 20, although not shown, may be angled or curved outwardly from each of upper plate 16 and lower plate 18 toward a location between upper plate 16 and lower plate 18.

In the particular arrangement being described, upper plate 16, lower plate 18 and bellows shaped shell 20 are formed unitarily as a one-piece bellows shaped spinal implant 10. More particularly in this arrangement, bellows shaped spinal implant 10 is formed of titanium. As noted hereinabove, titanium has desirable implant properties including biocompatibility, strength and osteointegration capability. While lack of radiolucency and relatively high stiffness may be considered drawbacks when considered against polymers such as polyetheretherketone (PEEK), such deficiencies are offset by the hollow bellows configuration of spinal implant 10. It has been found, for example, that when wall 22 of bellows shaped shell 20 is formed to have a thickness of approximately 0.5 mm radiographic imaging is achievable through wall 22 into hollow interior 24. Such imaging would tend to degrade with increased thickness, likely resulting in a loss of the radiographic benefit with a wall thickness greater than about approximately 1.0 mm. In addition, a wall thickness of less than approximately 0.5 mm may detrimentally weaken spinal implant 10 as well as potentially impacting manufacturability.

In addition to the benefit of radiolucency, the hollow bellows configuration of spinal implant 10 provides a beneficial impact on desired stiffness. It has been found that the thin walled hollow bellows shell 20 allows a degree of flexibility to spinal implant 10 by inducing bending stresses when the implant 10 is under compression. Such induced bending tends to reduce stiffness. The stresses in wall 22 as a result of such bending vary as a function of the angle beta, β for an inwardly curved wall 22. The more acute the angle beta, β, the more bending stresses occur and less direct compression occurs through wall 22. In turn, higher levels of deflection occur in configurations when the angle beta, β is more acute, tending to weaken the structure and making it less stiff. It is known that low stiffness promotes load sharing in accordance with Wolfs law with bone graft material contained in hollow interior 24. From a stiffness standpoint, the angle beta, β of inwardly curved wall of shell 20 may range from a minimum of approximately 0° to a maximum of approximately 180°. However, in some instances and sizes of spinal implant 10 having an inwardly curved wall 22, overly acute angles may be less desirable as excessive inward projection of the walls 22 would result in loss of internal volume for bone graft and may tend to decrease the stability of implant 10. Similarly, angles above 180° may be used to provide a similar effect regarding stiffness characteristics with an outwardly curved wall 22. However, angles above 180° may be less desirable due to the increased overall dimensions of the implant compared to the dimension of the contact surface, thereby requiring a larger entry corridor for implantation. It should be appreciated that a similar effect could be achieved without increasing the implant dimensions using angles above 180° if the wall 22 joins upper plate 16 and lower plate 18 at a location inset from the edges of upper plate 16 and lower plate 18. It should now be appreciated that walls 22 having appropriate inward or outward curvature may be utilized to effectively control implant stiffness.

It is noted that the angle beta, β may vary as a function of implant height to maintain desired stiffness characteristics. Shorter height implants would typically require more acute angles than taller heights due to the relationship between height and stiffness. Taller implants would typically be relatively less stiff so less acute angles would be needed to reduce stiffness A spinal implant 10 having an angle beta β, for example, of approximately 180° would result from a shell wall 22 being relatively straight. Such an implant may be made to have a height and wall thickness that would provide sufficient resiliency to reduce implant stiffness and may be used in spinal procedures, such as cervical corpectomies.

Further to the beneficial impact on radiolucency and low stiffness, the formation of bellows shaped spinal implant 10 from titanium allows for the promotion of rapid fixation of spinal implant 10 to endplates 12a and 14a of vertebral bodies 12 and 14. For example, contact surfaces 16a and 18a of upper plate 16 and lower plate 18, respectively, may be readily altered to enhance bone apposition by a 3-D printing process that would provide a porous surface with micro roughness. Such pores would be in communication with hollow interior 24 for through growth fusion of bone graft to vertebral endplates 12a and 14a. Additionally, the micro roughness of contact surfaces 16a and 18a may then be further augmented to add a nano roughness surface by laser ablation using, for example, a femto-second laser process.

Alternatively, an acid etching process could be used to alter the roughness of contact surfaces 16a and 18a to include micro and nano roughness. Furthermore, the contact surfaces 16a and 18a may be modified to alter the micro and nano-roughness by a combination nano-second and femto-second laser process, or by the femto-second laser process alone by varying selected parameters, such as the pulse duration or frequency of the laser process, or the quantity of energy applied. Accordingly, the desired surface roughness may be achieved by various methods, including without limitation, laser ablation, acid etching or a combination of both.

In one example of bellows shaped spinal implant 10 that is particularly configured for use as an ALIF device, the anterior height as depicted in FIG. 5 may range from 8 to 20 mm and the posterior height may range from 4 to 16 mm. As observed from FIG. 4, the anterior/posterior depth may range from 22 to 30 mm and the medial/lateral width may range from 24 to 42 mm. The thickness of shell wall 22 may be approximately 0.5 mm and the angle beta, β of bellows shaped shell 20 may be approximately 90°. A plurality of spinal implants 10 having different sizes and dimensions may be provided in a kit to allow the spinal surgeon to select the appropriate spinal implant 10 based upon the surgical needs and the anatomy of the patient. Prior to such selection, one or more trial devices simulating the size and configuration of a spinal implant 10 needed for a particular surgery may be provided. Once a proper spinal implant 10 is determined and chosen, it may be inserted into the lumbar spine between vertebral bodies 12 and 14 by attaching a portion of a suitable threaded inserter into threaded hole 26 of spinal implant 10. Spinal implant 10 is then manually urged by such inserter from an anterior direction between endplates 12a and 14a to the position shown in FIGS. 1 and 2. In some instances, bone graft may be prepacked into hollow interior 24 prior to insertion. In other instances, and subsequent to the removal of the threaded inserter, bone graft may be introduced into hollow interior 24 through threaded hole 26. In other instances, bone graft may be both prepacked into hollow interior 24 with additional bone graft introduced through threaded hole 26 into hollow interior 24 after insertion. As a result of the construction of bellows shaped shell 20, radiographic images of bone graft contained within hollow interior 24 may be taken by fluoroscopy or other suitable imaging devices through wall 22 subsequent to surgery so as to monitor the progress of fusion to endplates 12a and 14a of vertebral bodies 12 and 14, respectively.

Having described the details of bellows shaped spinal implant 10 herein, it should be appreciated that when formed of titanium, bellows shaped spinal implant 10 may be used as interbody device that mimics the desirable properties of a similarly sized PEEK implant while maintaining the benefits of titanium, such as strength and osteointegration capability. In addition, low stiffness as provided by bellows shaped implant 10 assists in mimicking the biomechanical properties of the spine to help promote uniform endplate contact and load sharing with bone graft.

Figure 9:
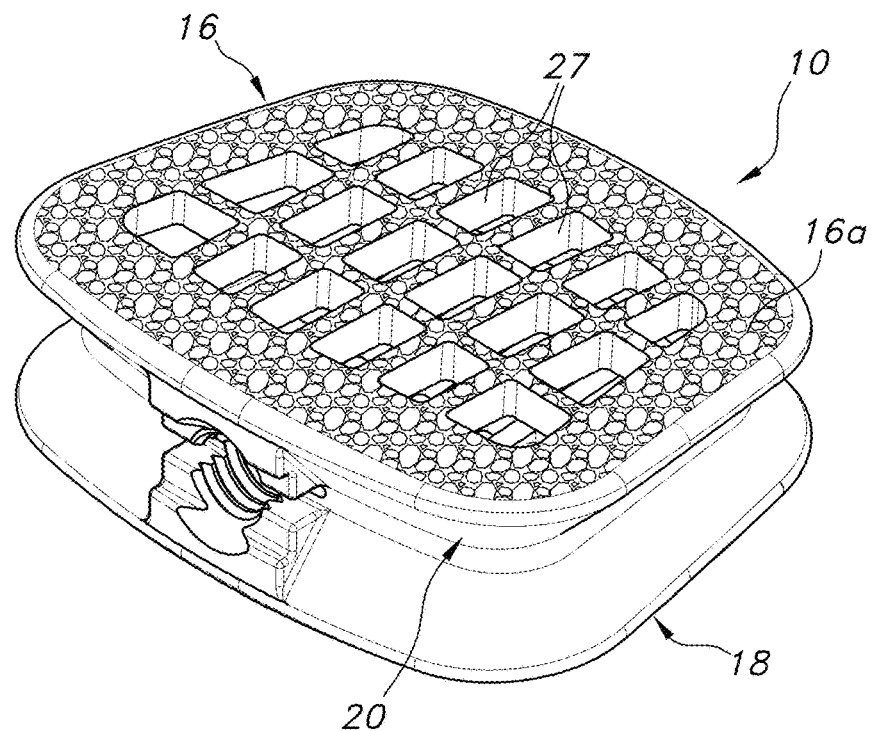
FIG. 9 is a top perspective view of a variation of the bellows shaped ALIF as seen from the anterior direction.
Figure 10:
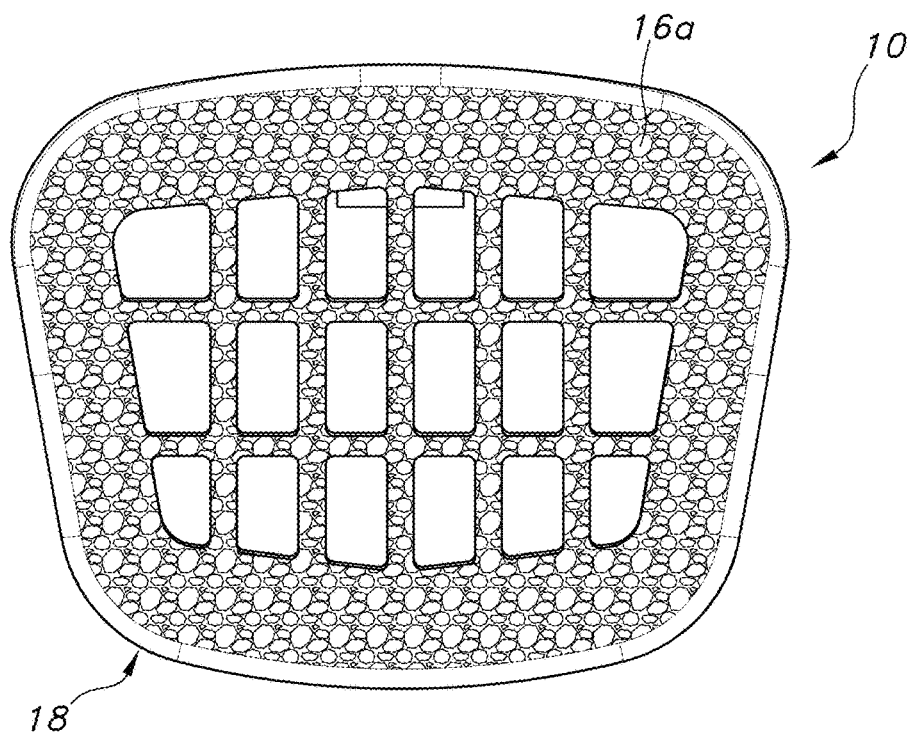
FIG. 10 is a top plan view of the bellows shaped ALIF device of FIG. 9.

While a preferred embodiment of bellows shaped spinal implant 10 as described herein is formed of pure titanium, it should also be appreciated that titanium alloys may also be used with similar beneficial results. Further, it should be understood that other variations may be made within the contemplated scope of the invention. For example, as shown in FIGS. 9 and 10, upper plate 16 and lower plate 18 of bellows shaped spinal implant 10 may be formed to have a plurality of fenestrations or smaller holes 27 instead of, or in addition to, single central openings 16b and 18b. Such holes 27 will still permit fusion therethrough of interior bone graft material to vertebral body endplates 12a and 14a, while the increased surface area of contact surfaces 16a and 18a will allow increased implant strength and enhanced contact surface area to vertebral body endplates 12a and 14a.

Figure 11:
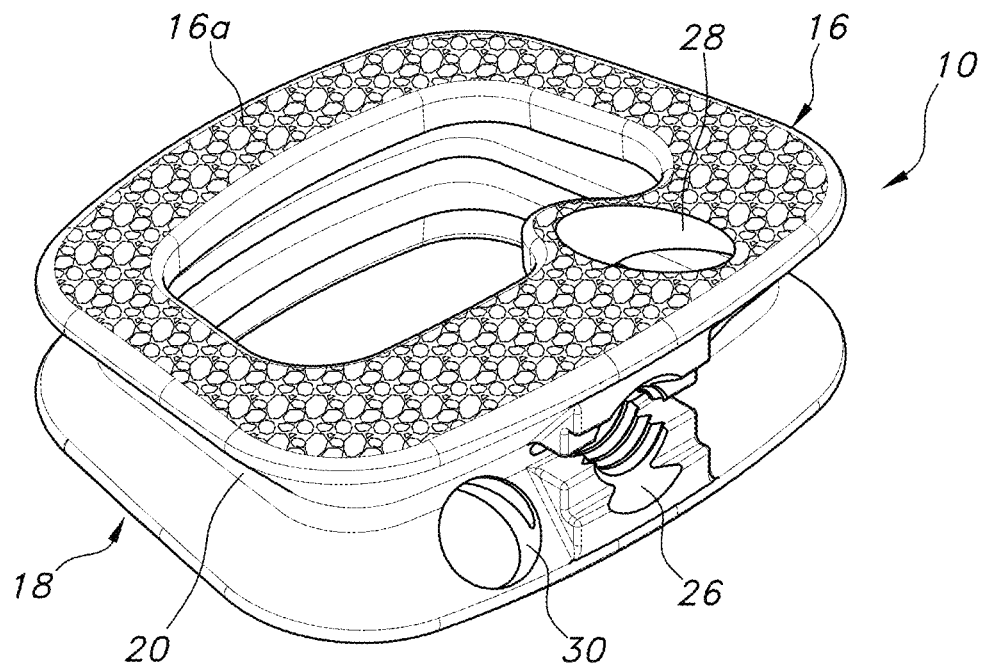
FIG. 11 is a top perspective view of further variation of the bellows shaped ALIF configured as a stand-alone device as seen from the anterior direction.
Figure 12:
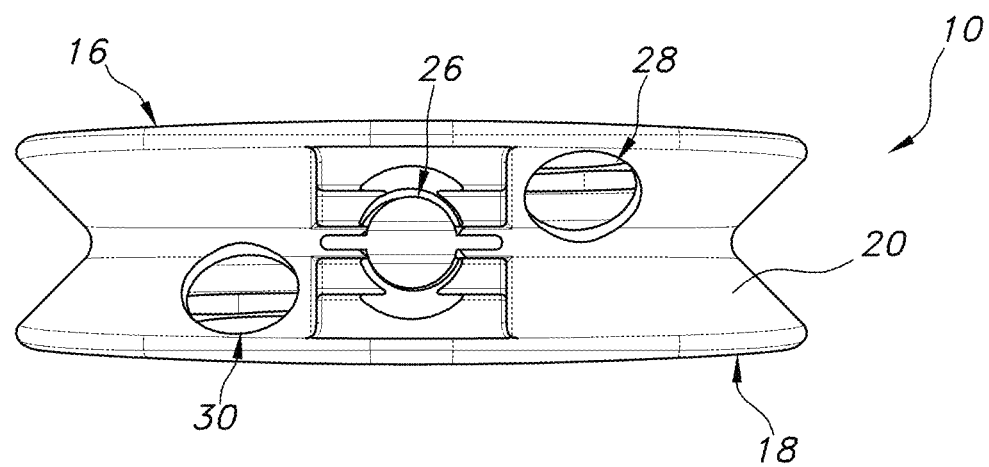
FIG. 12 is an anterior elevation view of the stand-alone bellows shaped ALIF device of FIG. 11.
Figure 13:
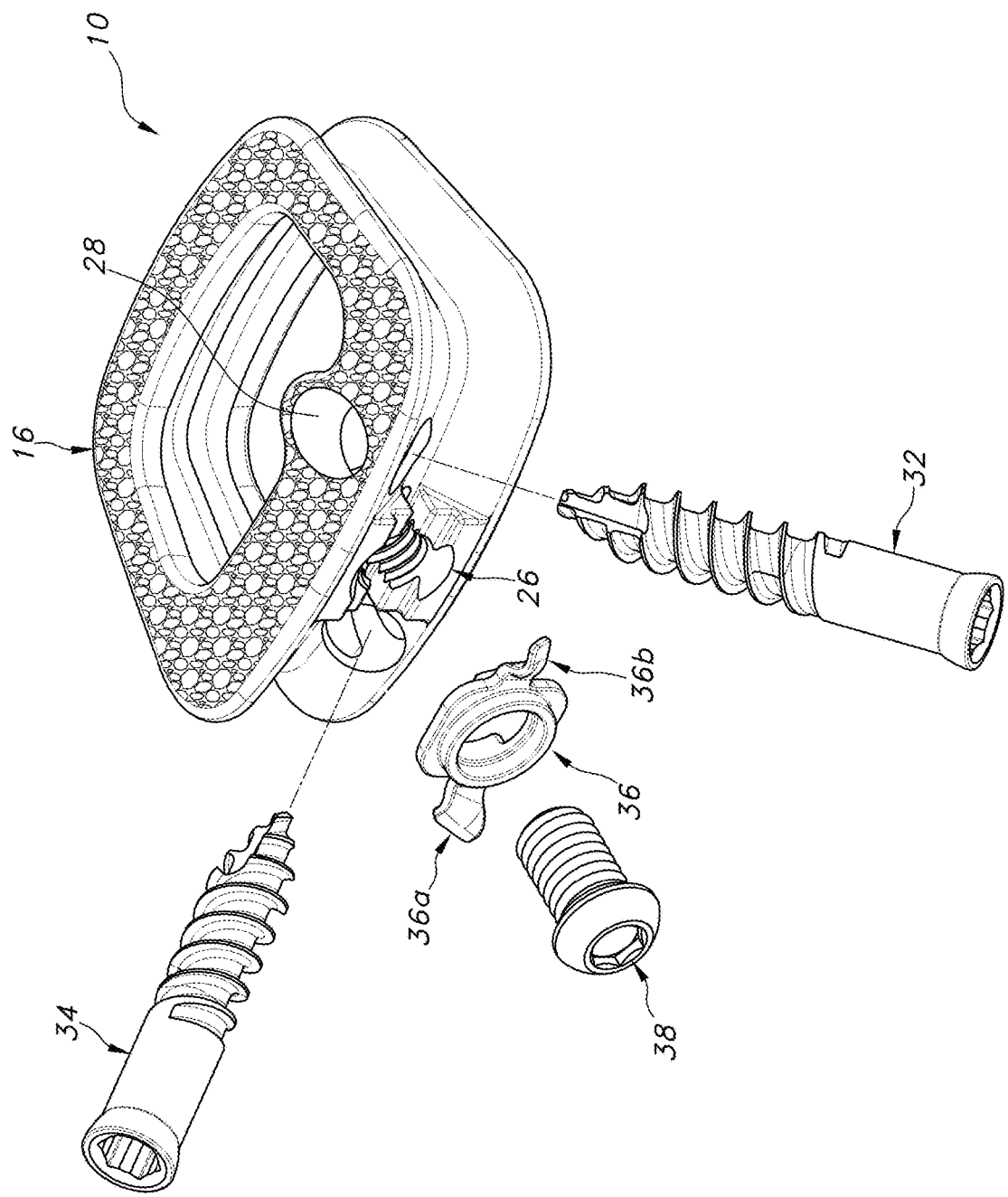
FIG. 13 is a top, anterior perspective view of the stand-alone bellows shaped ALIF device of FIG. 11 with exploded fixation screws and locking elements.

While bellows shaped spinal implant 10 has been described hereinabove as a conventional ALIF device for use with supplemental fixation, bellows shaped spinal implant 10 may also be configured as a stand-alone device. As shown in FIGS. 11 through 13, upper plate 16 and lower plate 18 may be formed to have fixation openings 28 and 30 angularly formed therethrough adjacent threaded hole 26 for receipt of fixation screws 32 and 34, respectively. Fixation screws 32 and 34 may be threadably attached to vertebral body endplates 14 and 12 through openings 28 and 30, respectively. A suitable locking element 36 comprising oppositely extending projections 36a and 36b may be provided to prevent fixation screws 32 and 34 from backing out subsequent to implant insertion. Locking element 36 may be attached to bellows shaped spinal implant 10 by a suitable locking screw 38 that is threaded into threaded opening 26 of spinal implant 10. Upon attachment of locking element 36 to spinal implant 10 by locking screw 38, projections 36a and 36b are configured to overlie fixation screws 32 and 34, respectively, in a manner to keep fixation screws 32 and 34 from backing out of vertebral bodies 12 and 14. Locking element 36 and locking screw 38 may be formed of PEEK material so as to minimize imaging artifacts and to maintain a desired stiffness of spinal implant 10.

Figure 14:
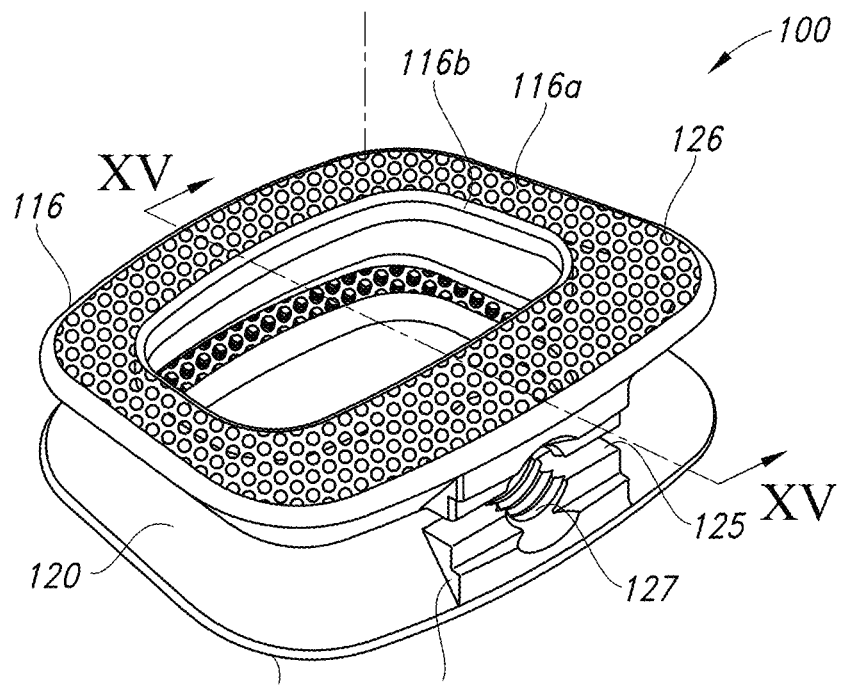
FIG. 14 is a top perspective view of an alternative bellows shaped ALIF device formed to have porous contact regions comprising gyroid lattice structures.
Figure 15:
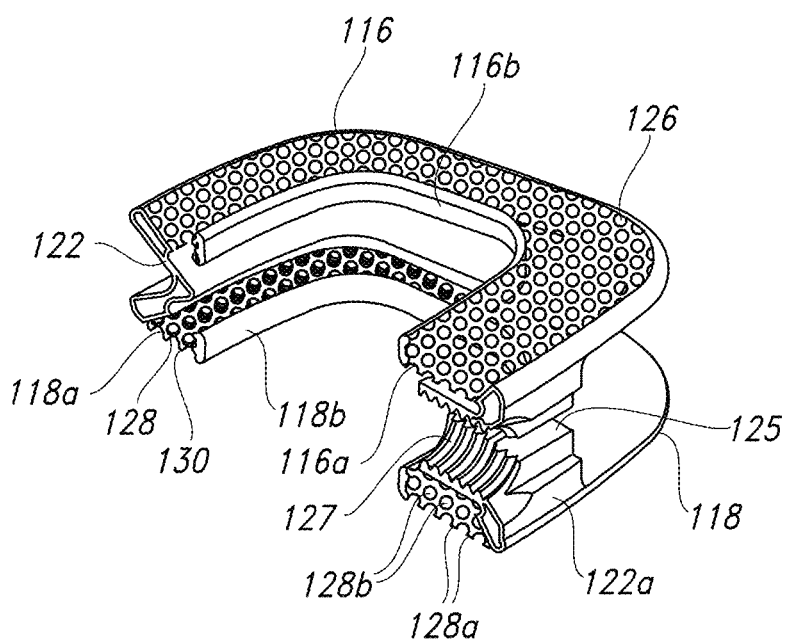
FIG. 15 is sectional view of the alternative bellows shaped ALIF device as seen along viewing lines XV-XV of FIG. 14.
Figure 16:
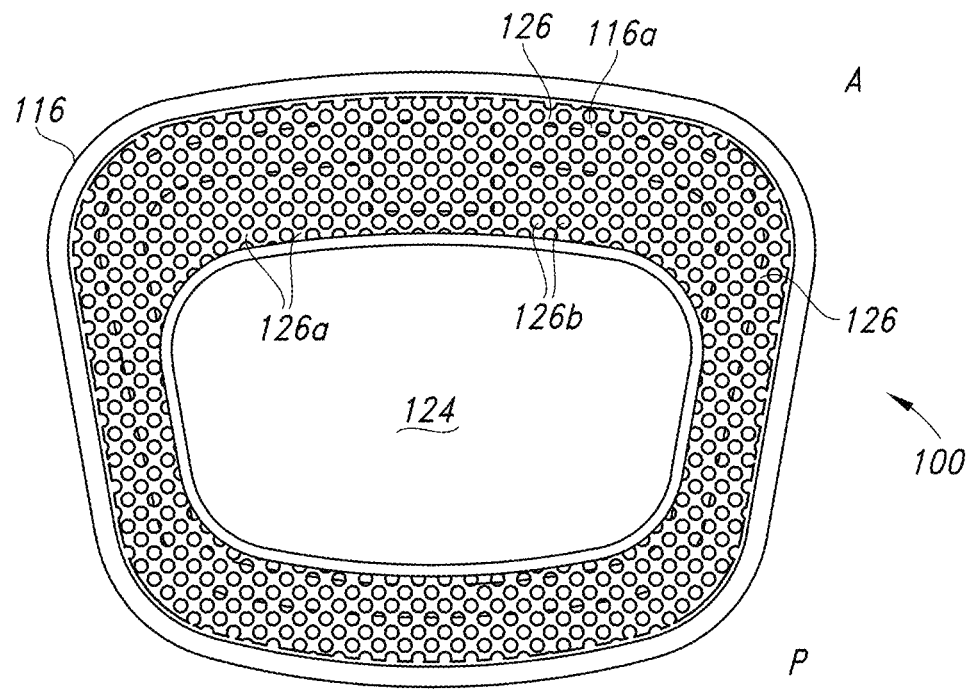
FIG. 16 is a top view of the alternative bellows shaped ALIF device of FIG. 14.
Figure 17:
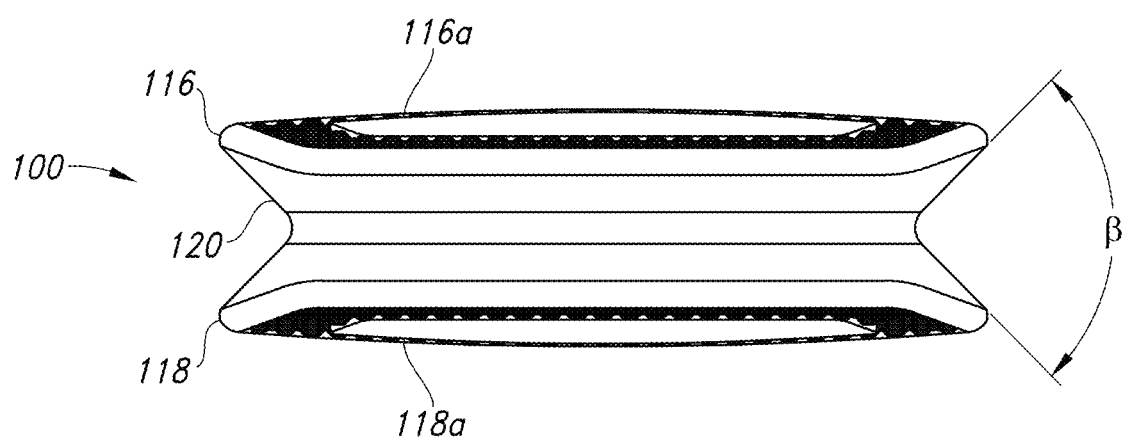
FIG. 17 is a posterior elevation view of the alternative bellows shaped ALIF device of FIG. 16.

Turning now to FIGS. 14-17, a further variation of the inventive bellows shaped spinal implant is described. In this exemplary variation, bellows shaped spinal implant 100 is a conventional ALIF device similar to bellows shaped implant 10 described above. As such, spinal implant 100 comprises an upper plate 116, a lower plate 118, and a bellows shaped shell 120 extending between and joining upper plate 116 and lower plate 118. Upper plate 116 and lower plate 118 may each have a quadrilateral perimeter with a respective central opening 116b, 118b extending therethrough. Such quadrilateral perimeter may be generally trapezoidal or rectangular. Shell 120 is likewise configured to have a bellows shape having a relatively thin wall 122 extending around the periphery of shell 120, wall 122 defining a hollow interior 124. Hollow interior 124 provides a space for bone graft material and is in fluid communication with central opening 116b of upper plate 116 and with central opening 118b of lower plate 118. Wall 122 is angled or curved inwardly between upper plate 116 and lower plate 118 and flares outwardly in both directions toward upper plate 116 and lower plate 118, respectively. As such as shown in FIG. 17, an inclusive bellows angle beta, β is formed in wall 122. Except as noted hereinbelow, the materials, dimensions and configuration of spinal implant 100 are the same as described and shown regarding spinal implant 10, including the thickness of wall 122 being within the range of 0.5 mm to 1.0 mm. Inclusive angle beta, β is the angle at which stiffness is minimized without compromising strength, with such preferred angle depending upon implant height. The inclusive angle beta, β may be within a range of approximately 0° to a maximum of approximately 180° and, in some instances, within a range of. approximately 69° to approximately 120°. The thickness of each of the upper plate 116 and the lower plate 118 may range from about 0.5 mm to 5.0 mm, more preferably from 1.0 mm to 3.0 mm, and particularly be about 2 mm. Wall 122 may be provided with a relatively thicker portion 122a at the anterior (A) end as shown in FIGS. 14 and 15 through which a threaded hole 127 may be formed for insertion and graft delivery purposes. In some instances, a suitable slit 125 or cut may be provided laterally into thicker portion 122a so as to minimize stiffening of implant 100.

In accordance with this variation, upper plate 116 comprises a porous contact region 116a for contacting a vertebral body within an intradiscal space of a spine, and lower plate 118 defines a porous contact region 118a for contacting an opposing vertebral body within the intradiscal space. Each of the porous contact regions 116a, 118a comprises a three-dimensional gyroid lattice structure 126, 128 as shown in FIGS. 14 and 15, defined by a plurality of struts 126a, 128a and pores 126b, 128b. One or more pores 126b, 128b extend through the respective porous contact regions 116a, 118a in communication with hollow interior 124. An outer surface of at least a portion of struts 126a, 128a may comprise a laser ablated textured surface, as will be described.

In this particular variation, the entire spinal implant 100, including upper plate 116, lower plate 118 and bellows shaped shell 120 is formed of titanium or a titanium alloy in an additive manufacturing process to form an integral structure. Such an additive manufacturing process allows for the formation of complex geometric structures, such as gyroid lattice structures 126, 128, providing greater design flexibility and minimizing waste. In a particular approach, the spinal implant 100 is formed by a 3-D printing process, although other additive manufacturing processes, such as direct metal laser sintering (DMLS) and electron beam melting (EBM) may also be used. In a particular formation, while porous contact regions 116a, 118a are formed to have gyroid lattice structures 126, 128, bellows shaped shell 120 is formed as a solid, non-porous structure. Details of the formation of the gyroid lattice structures 126, 128 are more fully described, for example, in U.S. Patent Publication No. 2021-0316367, entitled "Fabrication of Porous Scaffolds Using Additive Manufacturing with Potential Applications in Bone Tissue Engineering", published by Padilla et al. on Oct. 14, 2021, and in "Synthetic Bone: Design by Additive Manufacturing", Acta Biomaterialia, Vol. 97 (2019), pgs. 637-656, the entire contents of these references being incorporated by reference herein. In a particular arrangement, gyroid lattice structures 126, 128 are formed by an additive manufacturing process to have a skeletal architecture comprising a TPMS-based cellular scaffold. Struts 126a, 128a may have a thickness in the range of 0.25 mm-0.35 mm, pores 126b, 128b may each have s size in the range of 0.30 mm-0.60 mm, porosity may be a minimum of 75% and solid-lattice transition blend may be 0.20 mm. It should be appreciated that other dimensional aspects of gyroid lattice structures 126, 128 may be applicable.

Subsequent to the formation of spinal implant 100 by the additive manufacturing process, at least portions of the outer surfaces of gyroid structure struts 126a, 128a may be textured to enhance osteointegration in combination with gyroid lattice structures 116, 128. Textured surface may be produced in a geometric pattern having a plurality of projections and recesses 130 as depicted in FIG. 14. In a particular arrangement where spinal implant 100 is formed of titanium, texturing may be formed by ablating all or at least portions of the outer surfaces of struts 126a, 128a by a pulsed laser in the nanosecond range to create micro-scale structures comprising projections and recesses 130 having a depth of up to at least 100 μm. Such a process may be performed in accordance with the nanosecond laser devices and methods taught and described, for example, in U.S. Pat. No. 5,473,138, entitled "Method for Increasing the Surface Area of Ceramics, Metals and Composites", issued to Singh et al on Dec. 5, 1995, the entire contents of which are incorporated herein by reference.

In an effort to further enhance the tissue integration aspects gyroid lattice structures 126, 128 of a titanium spinal implant 100, texturing may be formed by ablating all or at least portions of the outer surfaces of struts 126a, 128a by an ultrafast pulsed laser to create smaller nano-structures comprising projections and recesses having a depth less than 1 μm and preferably not greater than 200 nm. Such a process may be preferably performed with a picosecond pulsed laser or, more preferably, with a femtosecond pulsed laser device in accordance with, for example, the methods and laser devices taught and described in U.S. Pat. No. 6,951,627, entitled "Method of Drilling Holes with Precision Laser Micromachining", issued October 2005 to Li et al., the entire contents of which are incorporated by reference herein. Other picosecond and femtosecond pulsed lasers may also be used, such as those described in U.S. Pat. No. 10,603,093, entitled "Bone Implant and Manufacturing Method Thereof", issued on Mar. 31, 2020 to Lin et al., the entire contents of which are incorporated herein by reference. It should be understood that the outer surfaces of struts 126a, 128a may be laser ablated by a combination of a nanosecond laser device and an ultrafast laser device, or by either laser device used separately, depending upon the surface texturing desired.

Figure 18:
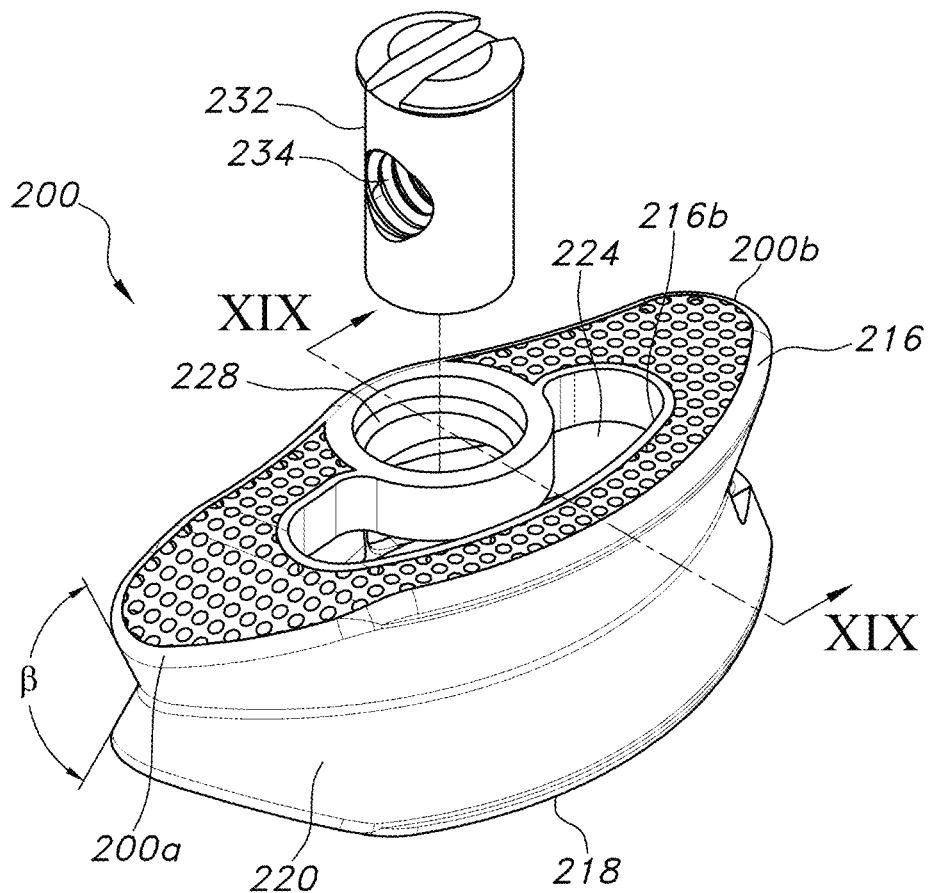
FIG. 18 is a top perspective exploded view of an alternative bellows shaped TLIF device formed to have porous contact regions comprising gyroid lattice structures.

Referring now to FIGS. 18-21, yet a further variation of the inventive bellows shaped spinal implant is described. In this exemplary variation, bellows shaped spinal implant 200 is particularly configured for use in transforaminal lumbar interbody fusion (TLIF) procedures. While a preferred embodiment of bellows shaped spinal implant 200 as described herein is formed of pure titanium, it should also be appreciated that titanium alloys may also be used with similar beneficial results. Spinal implant 200 comprises an upper plate 216, a lower plate 218, and a bellows shaped shell 220 extending between and joining upper plate 216 and lower plate 218. Upper plate 216 and lower plate 218 each have an arcuate generally oblong perimeter with a respective central opening 216b, 218b extending therethrough. Shell 220 is configured to have a bellows shape having a relatively thin wall 222 extending around the majority of the periphery of shell 220, wall 222 defining a hollow interior 224. Hollow interior 224 provides a space for bone graft material and is in fluid communication with central opening 216b of upper plate 216 and with central opening 218b of lower plate 218. Wall 222 is angled or curved inwardly between upper plate 216 and lower plate 218 and flares outwardly in both directions toward upper plate 216 and lower plate 218, respectively. As such as shown in FIG. 18, an angle beta, β is formed in wall 222. As described above regarding spinal implants 10 and 100, in bellows shaped spinal implant 200 the thickness of wall 222 of bellows shaped shell 222 is within a range of 0.5 mm to 1.0 mm. The inclusive angle beta, β of bellows shaped shell 220, which may vary with variation in height, may be in the range of approximately 124° to 156°.

Figure 19:
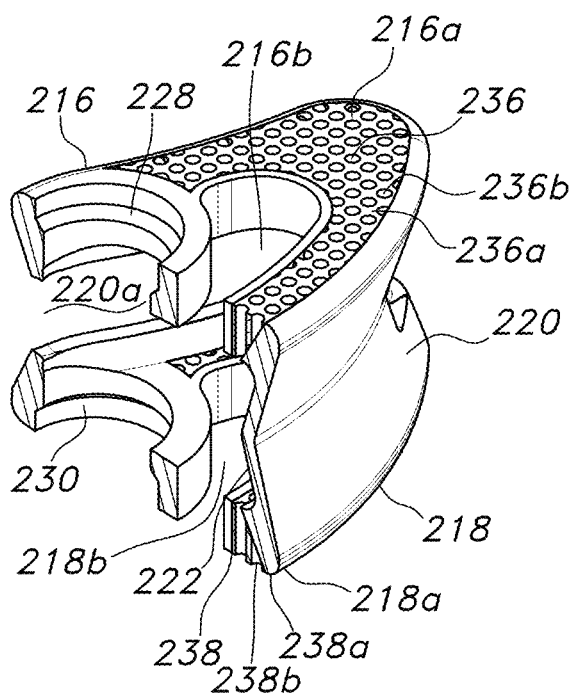
FIG. 19 is sectional view of the alternative bellows shaped TLIF device as seen along viewing lines XIX-XIX of FIG. 18.
Figure 20:
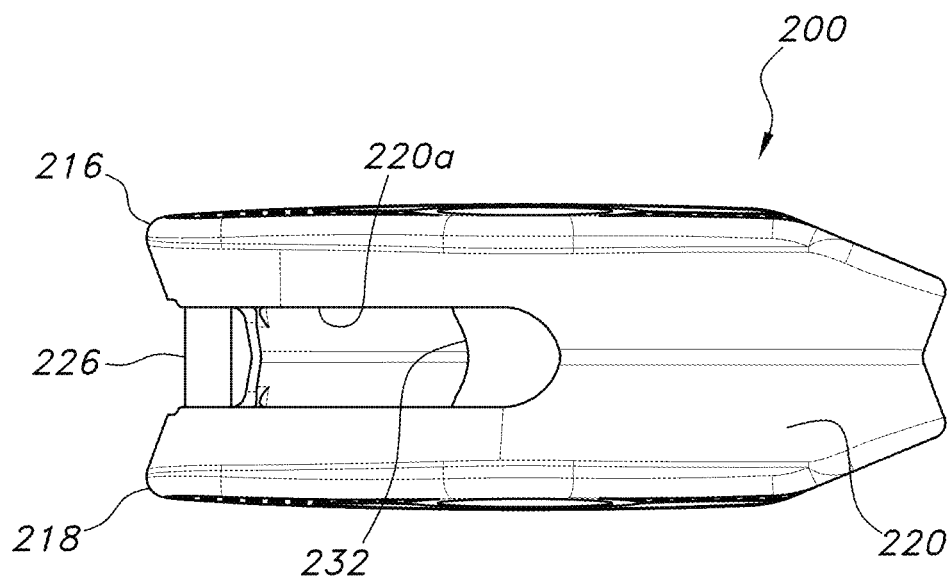
FIG. 20 is a side elevation view of the alternative bellows shaped TLIF device of FIG. 18.
Figure 21:
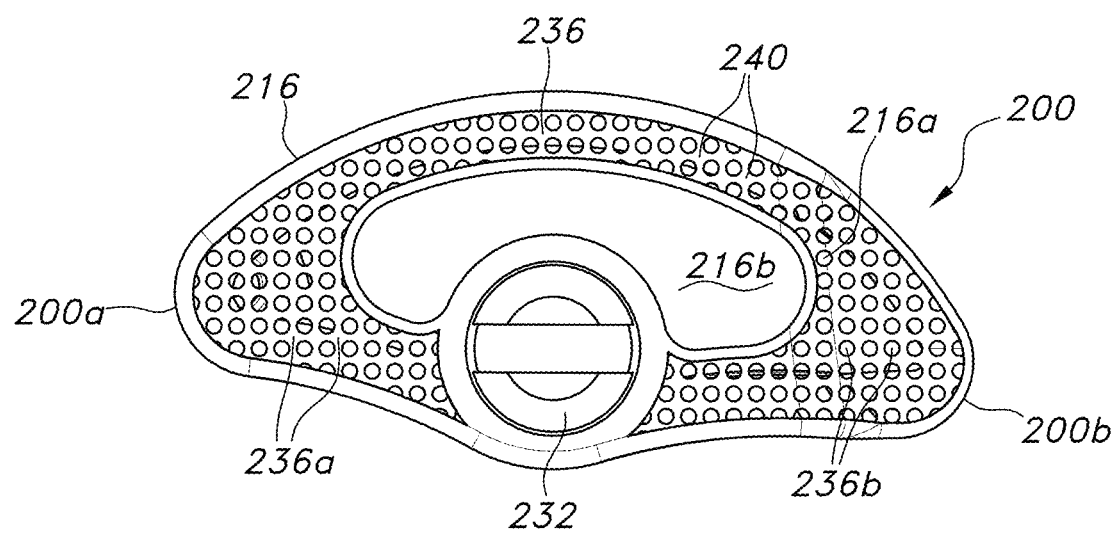
FIG. 21 is a top plan view of the alternative bellows shaped TLIF device of FIG. 18.

As seen more particularly in FIGS. 20 and 21, spinal implant 200 includes a first curved end 200a and a second opposite curved end 200b. In some instances, as shown in FIG. 18, upper plate 216 and lower plate 218 may be generally planar and angled downwardly from the curved end 200b toward curved end 200a so as to provide desired lordosis. In such a lordotic implant, bellows angle beta, β at curved end 200a may be less than angle beta, β at opposite curved end 200b. Bellows shaped shell 220 has a cutout portion 220a at first curved end 200a as shown in FIGS. 19 and 20. Spinal implant 200 includes a fixed post 226 disposed adjacent first curved end 200a, fixed post 226 extending between upper plate 216 and lower plate 218 and being accessible through cut-out portion 220a of shell 220, for purposes of which will be explained. Spinal implant 200 further includes an upper opening 228 extending through upper plate 216 and a lower opening 230 extending through lower plate 218. A pivot post 232 is disposed within upper opening 228 and lower opening 234 for rotatable movement within spinal implant 200. Pivot post 232 includes a threaded aperture 234 for receipt of a threaded portion of an insertion tool as will be described. Pivot post 232 is accessible for receipt of the threaded portion of the insertion tool through cutout portion 220a of shell 220.

In this particular variation, upper plate 216, lower plate 218 and bellows shaped shell 220 are integrally formed in an additive manufacturing process as described above regarding spinal implant 100. While fixed post 226 may also be produced by the additive manufacturing process, it may alternatively be formed separately and subsequently press fit into spinal implant 200. Further, pivot post 232 is separately formed, for example, by machining and is subsequently assembled into implant 200. In accordance with this variation as shown in FIGS. 19 and 21, upper plate 216 includes a porous contact region 216a for contacting a vertebral body within an intradiscal space of a spine, and lower plate 218 includes a porous contact region 218a for contacting an opposing vertebral body within the intradiscal space. Each of the porous contact regions 216a, 218a comprises a three-dimensional gyroid lattice structure 236, 238 defined by a plurality of struts 236a, 238a and pores 236b, 238b. One or more pores 236b, 238b extend through the respective porous contact regions 216a, 218a in communication with hollow interior 224. Gyroid lattice structures 236, 238 have, in a particular arrangement, the same dimensional characteristics as described above regarding lattice structures 126, 128.

Subsequent to the additive manufacturing of gyroid lattice structures 236, 238, an outer surface of at least a portion of struts 236a, 238a may be textured in accordance with the laser ablation processes described above with respect to spinal implant 100 to enhance osteointegration in combination with gyroid lattice structures 236, 238. Such textured surfaces may be produced in a geometric pattern having a plurality of projections and recesses 240 as illustrated in FIG. 21 that have the same characteristics and dimensions as projections and recesses 130 formed in spinal implant 100 as described above.

In one example of bellows shaped spinal implant 200 200 that is particularly configured for use as a TLIF device, the height as observed in FIG. 20 may range from 8 mm to 15 mm. As observed from FIG. 21, the width may range from 9 mm to 15 mm, and the length from curved end 200a to opposite curved end 200b may range from 25 mm to 40 mm. The thickness of each of the upper plate 216 and the lower plate 218 may range from 1.0 mm to 3.0 mm. In a non-lordotic implant having a generally constant height of 8 mm, the bellows angle beta, β at curved end 200a as well as at curved end 200b may be approximately 125°. In a lordotic implant, having for example a 9 mm height, bellows angle beta, β at curved end 200a may be approximately 124° and angle beta, β at opposite curved end 200b may be approximately 138°. As such, with the largest and smallest angles, β being at opposite ends of spinal implant 200, upper plate 216 and lower plate 218 are tilted relative to each other in a manner to provide lordosis during use.

Turning now to FIGS. 22 and 22A, the placement of spinal implant 200 into the intradiscal space by an insertion tool 400 is described. Tool 400 comprises an elongate channel 402, a grip 404 and a handle 406 at the user, proximal end of channel 402. A threaded shaft 408 is threadably attached into threaded aperture 234 of pivot post 232 of spinal implant 200. A pivot arm 410 is movably supported by channel 402 and is operatively connected to grip 404. The distal end of pivot arm 410 is engaged with fixed post 226 of spinal implant 200. Tool 400 is used to introduce spinal implant 200 into the intradiscal space in a transforaminal approach. Upon reaching a location in the intradiscal space that the surgeon determines to be appropriate, grip 404 is actuated to move pivot arm 410 to thereby cause rotation of spinal implant 200 about pivot post 232. Spinal implant 200 may be further manipulated within the intradiscal space by movement of tool 400, if desired, by the surgeon. Additional details of insertion tool 400 and the insertion technique are described in U.S. Pat. No. 10,722, 376, entitled "Method of Positioning a Spinal Implant", issued to Matthew G. Baynham on Jul. 28, 2020, the entire contents of which are incorporated by reference herein.

While the invention has been illustrated and described in detail in the drawings and foregoing description, the same should be considered as illustrative and not restrictive in character. Accordingly, it is understood that only the preferred embodiments have been presented and that all changes, modifications and further applications that come within the spirit of the invention are desired to be protected.

What is claimed is:

1. A spinal interbody fusion device, comprising:
    a one-piece, unitary structure including a pair of opposing porous portions and a non-porous peripheral wall extending between and joining said pair of opposing porous portions,
    each porous portion comprising a contact surface configured to contact a respective endplate of opposing vertebral bodies within an intradiscal space of a spine, each contact surface including a micro roughness having a plurality of pores extending entirely through said respective and contact surface, a surface of at least a portion of each said micro roughness comprising an augmented surface that includes a nano roughness, said porous portions and said peripheral wall together defining a hollow interior of the one-piece, unitary structure that is configured to receive bone graft, pores of each contact surface being in fluid communication with said hollow interior, each porous portion comprising at least one opening separate from said pores of each contact surface and extending entirely through said respective porous portion, each said opening being in fluid communication with said hollow interior; and
    wherein said spinal interbody fusion device has a height extending along a height direction, and wherein each of said porous portions has a thickness in the height direction, said thickness of each porous portion ranging from 10% to 50% of said height of said spinal interbody fusion device.

2. The spinal interbody fusion device of claim 1, wherein each micro roughness is formed by a 3-D printing process defining said respective plurality of pores.

3. The spinal interbody fusion device of claim 2, wherein said augmented surface of each micro roughness is formed by laser ablation.

4. The spinal interbody fusion device of claim 3, wherein said laser ablation is conducted with a femto-second laser.

5. The spinal interbody fusion device of claim 2, wherein said augmented surface of each micro roughness is formed by acid etching to form said nano roughness.

6. The spinal interbody fusion device of claim 1, wherein said peripheral wall has a hole extending therethrough in communication with said hollow interior.

7. The spinal interbody fusion device of claim 6, wherein said hole extending through said peripheral wall is configured for one of receipt of an inserter for inserting said device into said intradiscal space or receipt of bone graft therethrough and into said hollow interior.

8. The spinal interbody fusion device of claim 1, wherein said contact surfaces of said pair of porous portions are formed at an angle relative to each other.

9. The spinal interbody fusion device of claim 1, wherein said spinal interbody fusion device comprises titanium or a titanium alloy.

10. The spinal interbody fusion device of claim 9, wherein said peripheral wall is formed as a shell having a thickness in the range of 0.5 mm to 1.0 mm.

11. The spinal interbody fusion device of 10, wherein said shell comprises a bellows shaped configuration that is angled or curved inwardly between said contact surfaces.

12. A spinal implant interbody fusion device, comprising:
    a one-piece, unitary structure including:
    an upper porous portion comprising a contact surface having an upper micro roughness for contacting an endplate of a vertebral body within an intradiscal space of a spine, said upper porous portion being formed by a 3-D printing process defining a plurality of pores extending through said upper porous portion, an upper opening fully bounded and separate from said pores through said upper porous portion and extending entirely through said upper porous portion, a surface of at least a portion of said upper micro roughness comprising an augmented surface that includes a nano roughness;
    a lower porous portion comprising a contact surface having a lower micro roughness for contacting an endplate of an endplate of an opposing vertebral body within an intradiscal space of a spine, said lower porous portion being formed by a 3-D printing process defining a plurality of pores extending through said lower porous portion, a lower opening fully bounded and separate from said pores through said lower porous portion and extending entirely through said lower porous portion, a surface of at least a portion of said lower micro roughness comprising an augmented surface that includes a nano roughness; and
    a non-porous peripheral wall extending between and joining said upper porous portion and said lower porous portion, said upper porous portion, said lower porous portion, and said peripheral wall together defining a hollow interior of the one-piece, unitary structure that is configured to receive bone graft, said opening through said upper porous portion, said opening through said lower porous portion, and pores of said respective porous portions being in fluid communication with said hollow interior; and
    wherein said spinal interbody fusion device has a height extending along a height direction, and wherein each of said porous portions has a thickness in the height direction, said thickness of each porous portion ranging from 10% to 50% of said height of said spinal interbody fusion device.

13. The spinal interbody fusion device of claim 12, wherein each nano roughness is formed by laser ablation with a femtosecond laser.

14. The spinal interbody fusion device of claim 12, wherein each nano roughness is formed by acid etching.

15. The spinal interbody fusion device of claim 12, wherein said peripheral wall comprises a bellows shaped shell that is angled or curved inwardly between said upper porous portion and said lower porous portion at an inclusive angle, $\beta$.

16. The spinal interbody fusion device of claim 15, wherein said spinal interbody fusion device comprises titanium or a titanium alloy, and wherein said peripheral wall has a thickness in the range of 0.5 mm to 1.0 mm.

17. The spinal interbody fusion device of claim 12, wherein said spinal interbody fusion device is configured for use in a cervical interbody fusion procedure.

18. The spinal interbody fusion device of claim 12, wherein said spinal interbody fusion device is configured for use in a lumbar interbody fusion procedure.

19. The spinal interbody fusion device of claim 18, wherein said spinal interbody fusion device is configured for use in an anterior lumbar interbody fusion (ALIF) procedure.

20. A spinal interbody fusion device, comprising:
a one-piece, unitary structure including:
a pair of opposing porous portions and a non-porous, bellows-shaped peripheral wall extending between and joining said pair of opposing porous portions, said peripheral wall including an insertion portion and an elongate cut extending laterally into said insertion portion;
each porous portion comprising a contact surface configured to contact a respective endplate of opposing vertebral bodies within an intradiscal space of a spine, each contact surface including a micro roughness having a plurality of pores extending entirely through said respective contact surface, a surface of at least a portion of each said micro roughness comprising an enhanced surface that includes a nano roughness, said porous portions and said peripheral wall together defining a hollow interior of the one-piece, unitary structure that is configured to receive bone graft, pores of each contact surface being in fluid communication with said hollow interior, each porous portion comprising at least one opening separate from said pores extending through each contact surface and larger than any of said pores extending through each contact surface, each said opening being in fluid communication with said hollow interior.

21. The spinal interbody fusion device of claim 20, wherein said insertion portion further includes a hole extending through said peripheral wall, said hole being configured for one of receipt of an inserter for inserting said device into said intradiscal space or receipt of bone graft therethrough into said hollow interior.

22. The spinal interbody fusion device of claim 21, wherein said elongate cut extends laterally from each side of said hole.

23. The spinal interbody fusion device of claim 20, wherein said spinal interbody fusion device has a height extending along a height direction, and wherein each of said porous portions has a thickness in the height direction, said thickness of each porous portion comprising at least 10% of said height of said spinal interbody fusion device.

24. A spinal interbody fusion device, comprising:
a monolithic, one-piece, unitary structure including a pair of opposing porous portions and a non-porous, bellows-shaped peripheral wall extending between and joining said pair of opposing porous portions, said peripheral wall having an insertion portion comprising an outer surface, said peripheral wall including an insertion feature extending into said insertion portion interiorly from said outer surface to facilitate introduction of said device into an intradiscal space of a spine;
each porous portion comprising a contact surface configured to contact a respective endplate of opposing vertebral bodies within said intradiscal space, each contact surface including a 3-D printed micro roughness having a plurality of pores extending entirely through said respective contact surfaces, a surface of at least a portion of each said micro roughness comprising a laser ablated enhanced surface that includes a nano roughness, said porous portions and said peripheral wall together defining a hollow interior of the unitary structure that is configured to receive bone graft, pores of each contact surface being in fluid communication with said hollow interior, each porous portion comprising at least one opening separate from said pores of each contact surface and larger than any of said pores extending through each contact surface, each said opening being in fluid communication with said hollow interior.

25. The spinal interbody fusion device of claim 24, wherein said insertion feature is a hole extending through said insertion portion in communication with said hollow interior.

26. The spinal interbody fusion device of claim 25, wherein said hole is threaded.

27. The spinal interbody fusion device of claim 24, wherein said insertion portion further has a thickness greater than another portion of said peripheral wall.

28. The spinal interbody fusion device of claim 24, wherein each of said openings extending through said respective pair of opposing porous portions and contact surfaces is fully bounded by portions of said respective contact surfaces.

29. The spinal interbody fusion device of claim 24, wherein said spinal interbody fusion device has a height extending along a height direction, and wherein each of said porous portions has a thickness in the height direction, said thickness of each porous portion comprising at least 10% of said height of said spinal interbody fusion device.

* * * * *